(12) United States Patent
Hanewinkel et al.

(10) Patent No.: US 8,550,816 B2
(45) Date of Patent: *Oct. 8, 2013

(54) MANDIBULAR MANIPULATOR AND RELATED METHODS

(75) Inventors: William H. Hanewinkel, Salt Lake City, UT (US); Michael B. Gleeson, Salt Lake City, UT (US)

(73) Assignee: Kosmo Technologies, LLC, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/556,086

(22) Filed: Jul. 23, 2012

(65) Prior Publication Data

US 2013/0023797 A1 Jan. 24, 2013

Related U.S. Application Data

(63) Continuation-in-part of application No. 13/130,517, filed as application No. PCT/US2010/001839 on Jun. 24, 2010, now Pat. No. 8,226,407, and a continuation of application No. PCT/US2012/022089, filed on Jan. 20, 2012.

(60) Provisional application No. 61/461,657, filed on Jan. 21, 2011, provisional application No. 61/269,344, filed on Jun. 24, 2009.

(51) Int. Cl.
*A61C 5/00* (2006.01)

(52) U.S. Cl.
USPC .......................................................... 433/140

(58) Field of Classification Search
USPC ......... 433/5, 24, 68, 140, 196, 214; 33/567.1, 33/162
See application file for complete search history.

(56) References Cited

U.S. PATENT DOCUMENTS 2,353,886 A * 7/1944 Findley et al. .................. 33/832
2,669,988 A    5/1951 Carpenter
(Continued)

FOREIGN PATENT DOCUMENTS

CA    2 189 174    10/1996
CA    2 236 456    10/1996
(Continued)

OTHER PUBLICATIONS

International Search Report PCT/US2010/001839 dated Mar. 31, 2011.

(Continued)

*Primary Examiner* — Cris L Rodriguez
*Assistant Examiner* — Matthew Saunders
(74) *Attorney, Agent, or Firm* — TraskBritt

(57) ABSTRACT

Described is a mandibular manipulator instrument as a standalone tool or with associated mouthpiece that includes two interlocking laterally sliding frames including a movable upper and a lower incisor pull, shaped for receiving a patient's central incisor teeth and a pair of pinion shafts for driving the upper and lower incisor pulls. A screw thread is used to provide a precise lateral motion for the sagittal measurement. The mouthpiece is constructed of resilient rubber. The manipulator is positioned and held in the resilient rubber mouthpiece by the two pinions protruding through acoustically tight apertures respective to each pinion's position. The manipulator can be used for other applications in an embodiment without the mouthpiece and/or in combination with a bite registration shape that is part of the manipulator frame.

20 Claims, 20 Drawing Sheets

(56) References Cited

U.S. PATENT DOCUMENTS

| | | | |
|---|---|---|---|
| 3,638,323 A * | 2/1972 | Groe | 33/567.1 |
| 4,148,308 A | 4/1979 | Sayer | |
| 4,283,173 A | 8/1981 | Browne et al. | |
| 4,425,911 A | 1/1984 | Luomanen et al. | |
| 4,439,147 A | 3/1984 | Magill et al. | |
| 4,472,140 A | 9/1984 | Lustig | |
| 4,495,945 A | 1/1985 | Liegner | |
| 4,602,905 A * | 7/1986 | O'Keefe, III | 433/41 |
| D288,346 S | 2/1987 | Walsh | |
| 4,806,100 A | 2/1989 | Schainholz | |
| 4,827,943 A | 5/1989 | Bornn et al. | |
| 4,828,418 A | 5/1989 | Sauer et al. | |
| 4,901,737 A | 2/1990 | Toone | 128/848 |
| 5,024,218 A | 6/1991 | Ovassapian et al. | |
| 5,086,768 A | 2/1992 | Niemeyer | |
| 5,154,608 A | 10/1992 | Feher | |
| 5,154,609 A * | 10/1992 | George | 433/68 |
| 5,199,872 A | 4/1993 | Leal | |
| 5,280,791 A | 1/1994 | Lavie | |
| 5,305,741 A | 4/1994 | Moles | |
| 5,313,960 A | 5/1994 | Tomasi | 128/848 |
| 5,365,945 A | 11/1994 | Halstrom | 128/848 |
| 5,374,237 A * | 12/1994 | McCarty, Jr. | 601/38 |
| 5,409,017 A | 4/1995 | Lowe | |
| 5,427,117 A | 6/1995 | Thornton | 128/848 |
| 5,537,994 A | 7/1996 | Thornton | 128/204.18 |
| 5,566,683 A | 10/1996 | Thornton | 128/848 |
| 5,570,704 A | 11/1996 | Buzzard et al. | 128/848 |
| 5,611,355 A | 3/1997 | Hilsen | 128/848 |
| 5,642,737 A | 7/1997 | Parks | 128/848 |
| 5,678,567 A * | 10/1997 | Thornton et al. | 128/848 |
| 5,755,219 A | 5/1998 | Thornton | 128/201.18 |
| 5,794,627 A | 8/1998 | Frantz et al. | 128/848 |
| 5,816,799 A | 10/1998 | Parker | 433/6 |
| 5,823,193 A | 10/1998 | Singer et al. | 128/848 |
| 5,826,579 A | 10/1998 | Remmers et al. | |
| 5,846,212 A * | 12/1998 | Beeuwkes et al. | 601/38 |
| 5,868,138 A | 2/1999 | Halstrom | 128/848 |
| 5,884,628 A | 3/1999 | Hilsen | 128/848 |
| 5,921,942 A | 7/1999 | Remmers et al. | 600/529 |
| 5,954,048 A | 9/1999 | Thornton | 128/201.18 |
| 5,983,892 A | 11/1999 | Thornton | 128/201.26 |
| 6,041,784 A | 3/2000 | Halstrom | 128/848 |
| 6,055,986 A | 5/2000 | Meade | 128/848 |
| 6,109,265 A | 8/2000 | Frantz et al. | 128/848 |
| 6,155,262 A * | 12/2000 | Thornton et al. | 128/859 |
| 6,161,542 A | 12/2000 | Halstrom | 128/848 |
| 6,183,423 B1 | 2/2001 | Gaumond et al. | |
| 6,244,865 B1 * | 6/2001 | Nelson et al. | 433/140 |
| 6,273,859 B1 | 8/2001 | Remmers et al. | |
| 6,305,376 B1 | 10/2001 | Thornton | 128/848 |
| 6,325,064 B1 | 12/2001 | Thornton | 128/204.18 |
| 6,374,824 B1 | 4/2002 | Thornton | 128/201.26 |
| 6,379,311 B1 | 4/2002 | Gaumond et al. | |
| 6,516,805 B1 | 2/2003 | Thornton | 128/848 |
| 6,634,353 B1 | 10/2003 | Knebelman et al. | 128/200.24 |
| 6,729,335 B1 | 5/2004 | Halstrom | 128/848 |
| 6,769,910 B1 | 8/2004 | Pantino | 433/6 |
| 6,877,513 B2 | 4/2005 | Scarberry et al. | 128/848 |
| 7,146,982 B2 | 12/2006 | Mousselon et al. | 128/848 |
| 7,174,895 B2 | 2/2007 | Thornton et al. | 128/848 |
| 7,328,698 B2 | 2/2008 | Scarberry et al. | |
| 7,328,705 B2 | 2/2008 | Abramson | 128/848 |
| 7,331,349 B2 | 2/2008 | Brady et al. | 128/848 |
| 7,357,635 B2 | 4/2008 | Belfor et al. | 433/24 |
| 7,364,429 B2 | 4/2008 | Olivier | |
| 7,448,388 B2 | 11/2008 | Halstrom | |
| 7,832,403 B2 | 11/2010 | Halstrom et al. | |
| 8,226,407 B2 * | 7/2012 | Hanewinkel et al. | 433/140 |
| 2001/0047805 A1 | 12/2001 | Scarberry et al. | |
| 2005/0028827 A1 * | 2/2005 | Halstrom | 128/861 |
| 2005/0081859 A1 | 4/2005 | Scarberry et al. | 128/206 |
| 2005/0175954 A1 * | 8/2005 | Zacher | 433/5 |
| 2007/0209666 A1 * | 9/2007 | Halstrom et al. | 128/859 |
| 2007/0264609 A1 | 11/2007 | Brunner et al. | |
| 2008/0072915 A1 * | 3/2008 | Nelissen | 128/848 |
| 2008/0105268 A1 | 5/2008 | Kusukawa | |
| 2008/0135056 A1 * | 6/2008 | Nelissen | 128/848 |
| 2010/0316973 A1 | 12/2010 | Remmers et al. | |

FOREIGN PATENT DOCUMENTS

| | | |
|---|---|---|
| EP | 1 832 306 | 9/2007 |
| WO | 97/16151 | 5/1997 |
| WO | 0152928 | 7/2001 |
| WO | 03092562 | 11/2003 |
| WO | 2006/070805 | 7/2006 |
| WO | WO 2010141868 A2 | 12/2010 |
| WO | WO 2010141868 A3 | 12/2010 |
| WO | 2011005299 | 1/2011 |
| WO | WO 2012100203 A2 | 7/2012 |

OTHER PUBLICATIONS

Written Opinion PCT/US2010/001839 dated Mar. 31, 2011.
PCT International Search Report for PCT/US2012/022089 dated Jul. 26, 2012.

* cited by examiner

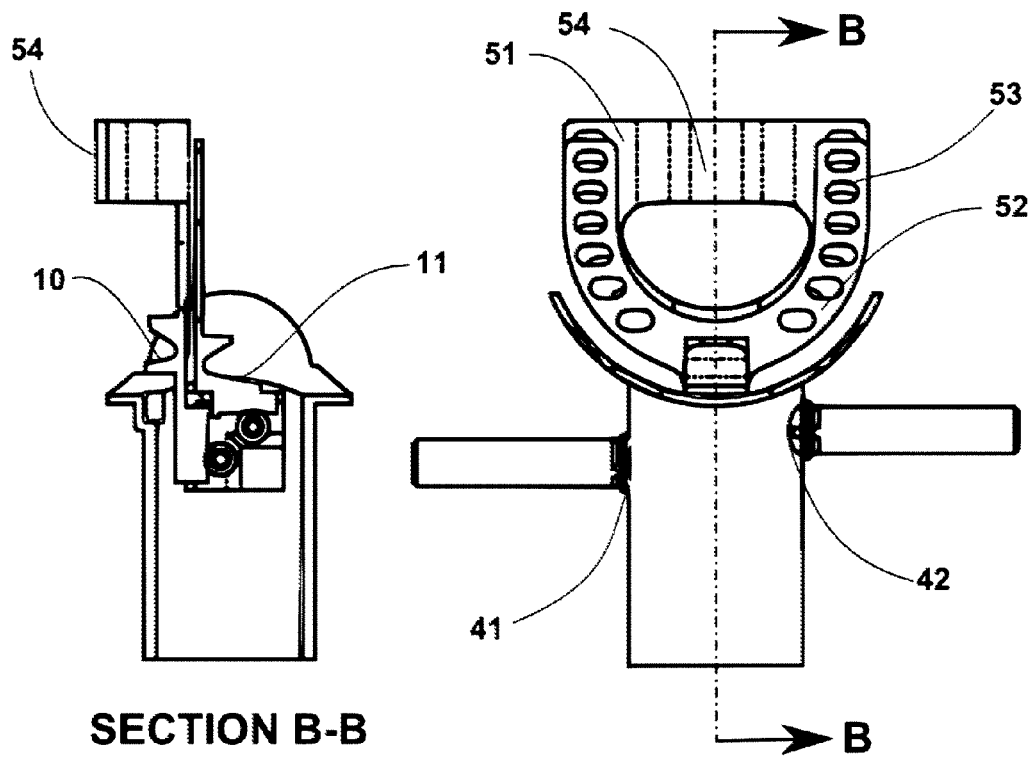
SECTION B-B
FIG. 7
FIG. 6
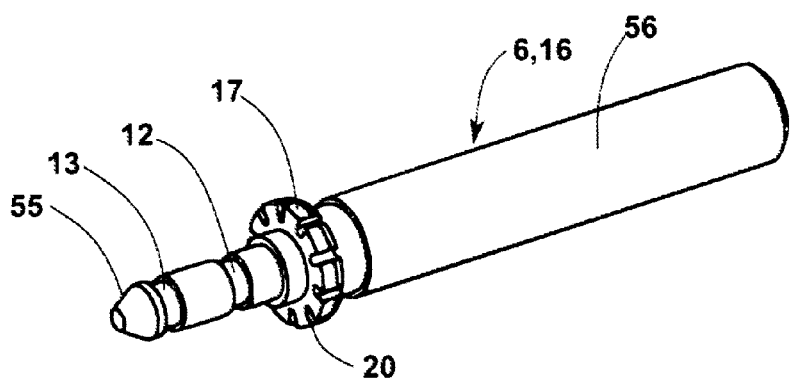
FIG. 8

MANDIBULAR MANIPULATOR AND RELATED METHODS

CROSS-REFERENCE TO RELATED APPLICATIONS

This application is a continuation-in-part of co-pending U.S. patent application Ser. No. 13/130,517, filed May 20, 2011, U.S. Pat. No. 8,226,407 (Jul. 24, 2012), which application is a national phase entry under 35 U.S.C. §371 of International Patent Application PCT/US2010/001839, filed Jun. 24, 2010, published in English as International Patent Publication WO 2011/005299 on Jan. 13, 2011, which claims the benefit under Article 8 of the Patent Cooperation Treaty and under 35 U.S.C. §119(e) to U.S. Patent Application Ser. No. 61/269,344, filed on Jun. 24, 2009, the disclosure of each of which is hereby incorporated herein in its entirety by this reference. This application is also a continuation of International Patent Application PCT/US2012/022089, filed Jan. 20, 2012, which claims the benefit under Article 8 of the Patent Cooperation Treaty and under 35 U.S.C. §119(e) to U.S. Patent Application Ser. No. 61/461,657, filed Jan. 21, 2011, the disclosure of each of which is hereby incorporated herein in its entirety by this reference.

TECHNICAL FIELD

This disclosure relates generally to medical and dental equipment, and more particularly relates to an instrument and associated methods used as an adjunct to instruments for diagnosing dental and medical problems associated with a patient's mandibular (jaw) position and requiring the accurate measuring of the mandible relative to the maxilla in three orthogonal dimensions.

BACKGROUND

The current state of the art for manipulating a patient's mandible includes the well-known George Gauge™. (See, for example, U.S. Pat. No. 7,448,388.) The George Gauge™ allows for the movement of the lower mandible only in the anteroposterior axis and minimal vertical change.

Several problems can occur with the current method of achieving desired mandibular position because the patient is instructed to, e.g., position their mandible as the dental/medical procedure is performed. In several instances, the current methodology is tried sequentially in set intervals while having to remove the instrument between setting of the mandible and recording the patient's bite registration. Present methods lack the precision and repeatability needed to analyze a patient in real time with any diagnostic instrument or during other dental procedures requiring mandibular manipulation. This trial-and-error method not only increases the diagnosis time, but prevents an accurate means of noting where the relative position of the mandible lies in relation to the maxilla. Consequently, the dental appliance created for the patient can sometimes need to be created several times before the appliance works correctly. And, in some cases, the patient becomes dissatisfied with the overall lack of good results and gives up.

A U.S. Patent search was conducted and the following patents were uncovered: U.S. Pat. No. 7,448,388 (Nov. 11, 2008) to Halstrom; U.S. Pat. No. 6,183,423 (Feb. 6, 2001) to Gaumond et al.; U.S. Pat. No. 6,379,311 (Apr. 30, 2002) to Gaumond et al.; U.S. Pat. No. 6,244,865 (Jun. 12, 2001) to Nelson et al.; U.S. Pat. No. 2,669,988 (May 8, 1951) to Carpenter; U.S. Pat. No. 4,148,308 (Apr. 10, 1979) to Sayer; U.S. Pat. No. 4,425,911 (Jan. 17, 1984) Luomanen et al.; U.S. Patent; U.S. Pat. No. 4,495,945 (Jan. 29, 1985) to Liegner; U.S. Pat. No. 5,024,218 (Jun. 18, 1991) to Ovassapian et al.; U.S. Pat. No. 5,086,768 (Feb. 11, 1992) to Niemeyer; U.S. Pat. No. D288,346 (Feb. 17, 1987) to Walsh; U.S. Pat. No. 5,305,741 (Apr. 26, 1994) to Moles; U.S. Pat. No. 4,828,418 (May 9, 1989) to Sauer et al.; U.S. Pat. No. 4,472,140 (Sep. 18, 1984) to Lustig; U.S. Pat. No. 4,806,100 (Feb. 21, 1989) to Schainholz; U.S. Pat. No. 7,364,429 (Apr. 29, 2008) to Olivier; U.S. Pat. No. 5,154,609 (Oct. 13, 1992) to George; U.S. Pat. No. 5,199,872 (Apr. 6, 1993) to Leal; and U.S. Pat. No. 4,439,147 (Apr. 17, 1984) to Magill and Key, the contents of the entirety of each of which are incorporated herein by this reference.

The inventors hereof have invented the mandibular manipulator described and claimed in PCT International Patent Application Publication WO/2011/005299 (published in English on Jan. 13, 2011), which patent application claims priority under Article 8 of the Patent Cooperation Treaty and 35 U.S.C. §119(e) to U.S. Provisional Application Ser. No. 61/269,344, filed on Jun. 24, 2009, the contents of the entirety of which are incorporated herein by this reference.

SUMMARY OF THE INVENTION

Described are instruments useful, for among other things, to diagnose dental and medical problems associated with a patient's mandible positioning and requiring the accurate measuring of the mandible relative to the maxilla in three dimensions. The instruments have mechanical features for engaging the incisor teeth of the maxilla and mandible, a mechanical connection between the mandible and maxilla engagement means, and calibrations provided on the connection for measuring relationships between the mandible and maxilla.

The mechanical connection between the mandible and maxilla engagement allows for a means of two self-retaining sliding incisor pulls that move perpendicular to one another and three rotating members to actuate the pulls. The incisor pulls have a self-retaining shape and also have a small protrusion at one end so as to prevent their leaving the guide slots once a device according to the invention is assembled for use. The mechanical connection allows for motion of the incisor sliding pulls in both an anterior/posterior direction and a vertical direction and a third mechanical connection is provided to allow sagittal or right and left relative motion of the incisor pulls. A locking means is provided for the anterior/posterior motion and the vertical motion to allow the ideal position to be held. The sagittal position is held by means of its thread/nut mechanism utilized for its positioning.

The instrument can either be utilized with our without a bite plate. When it is used with an impression plate, the plate has upper and lower planar surfaces for holding imprint materials, and the shape of the plate approximates the bite of the upper and lower teeth. Within this embodiment, the impression plate can be of different sizes and either be integral specifically to the sliding incisor pulls or be attached to the upper incisor pull by a retained "snap" feature or by other mechanical means to prevent its unintentional removal.

A threaded type of locking mechanism may be provided for the anteroposterior and the vertical motions and is used to fix the upper and lower incisor pulls in place.

Graduated scales or gradation markings or indicators are marked in the connecting frame of the instrument to accurately quantify the movement in both the anteroposterior, vertical axes as well as the sagittal movement. In another refined embodiment, the instrument allows for electronic feedback of the positions to be recorded by data logger or other computer recording, thus allowing for an automatic record of the mandible position.

Uses of this instrument can be applied to the diagnosing or troubleshooting associated with the causes of sleep apnea, temporomandibular joint dysfunction (TMD), problems associated with the temporomandibular joints (TMJ), or any concern related to the alignment of the mandible in relationship to the maxilla. Another application of this instrument is for a qualitative measurement using bite registry material when performing a dental procedure or medical procedure requiring an accurate relationship of the position of the mandible in relation to the maxilla.

Another embodiment is the use of remote movement of the instrument to achieve appropriate positioning of the mandible to open the airway in designing an oral appliance for a patient suffering from obstructive sleep apnea.

In yet another embodiment, the position of the mandible relative to the maxilla can be precisely measured or positioned while using electrodiagnostic equipment or radiology to realize the necessary location of the mandible, for creating a remedy for patients suffering from TMJ.

One use of the device is in the application of an acoustic oral pharyngometer instrument to measure the area and volume of the throat opening of a patient as he or she breathes. The simple motion of moving the lower mandible either anteroposterior and up and down, can help open the throat and ease breathing. The outcome of the procedure is to either create a dental appliance to use while the patient sleeps or for referral to another medical professional for further analysis of the patient's throat. Typically, a dental appliance is constructed from the resulting oral pharyngometer procedure and this is used to hold the mandible in a set position as the patient sleeps to prevent breathing difficulties. This invention allows the oral pharyngometer procedure to be performed in real time without having to sequentially remove the adjusting instrument.

The acoustic pharyngometer sees the mandibular manipulator as an object in the airway waveguide prior to the acoustic wave entering the patient's mouth and throat but does not attenuate the overall strength of the returning signal. Because the overall mouthpiece tube is longer in length, the anteroposterior distances are shifted the same distance in the pharyngometer readout but the relative distances of the incisors to the soft pallet and pharyngeal remain constant.

Another embodiment is the use of remote movement of the instrument to achieve appropriate positioning of the mandible to open the airway in designing an oral appliance for a patient suffering from obstructive sleep apnea.

In yet another embodiment, the position of the mandible relative to the maxilla can be precisely measured or positioned while using electrodiagnostic equipment or radiology to realize the necessary location of the mandible, for creating a remedy for patients suffering from TMJ.

Dentists and sleep apnea physicians would prefer to use an instrument that would quantify in a reliable, repeatable, and easy way the position of the mandible to the maxilla for real-time measurement in 3 planes from the most posterior to the most anterior and from the least vertical to the maximum vertical position paths, and from the sagittal centerline both left and right.

The mandibular manipulator operates by inserting the snorkel like mouthpiece into a patient's mouth and engaging the patient's upper and lower front teeth with the upper and lower manipulator incisor pulls. An acoustic pharyngometer or other medical instrument is attached to the open end of the mouthpiece and operated per the manufacturer's instructions. The mandibular manipulator is operated by rotation of the pinions either by hand or with small motors by computer feedback with the pharyngometer or medical instrument. The patient's mandible is manipulated by the two lifts until the mandible position is such that the ideal airway is shown by the medical instrument readout. The dentist may at this point apply a quick setting bite paste to provide an impression for the creation of a dental appliance.

DESCRIPTION OF THE DRAWINGS

FIG. 6 is a top view of a device according to the invention.

FIG. 7 is a cross sectional view B-B of FIG. 6.

FIG. 8 is a perspective view of the pinion element.

BEST MODE(S) FOR CARRYING OUT THE INVENTION

The following terminology is used herein:

Dental Articulator: Mechanical instruments that simulate the temporomandibular joints and jaws to which maxillary and mandibular casts are attached. The entire assembly attempts to reproduce the movements of the mandible and the various tooth-to-tooth relationships that accompany those movements.

Maxilla: anatomy: of a pair of bones of the human skull fusing in the mid line and forming the upper jaw.

Dental: The irregularly shaped bone forming half of the upper jaw. The upper jaw is made up of the two maxillae.

Incisal edges of the lower to upper central incisor teeth.

Anteroposterior: Anatomical term referring to an axis and for the purpose of this application defines an axis from front to back of the mouth.

Sagittal: A vertical plane passing through the standing body from front to back.

Figure 1:
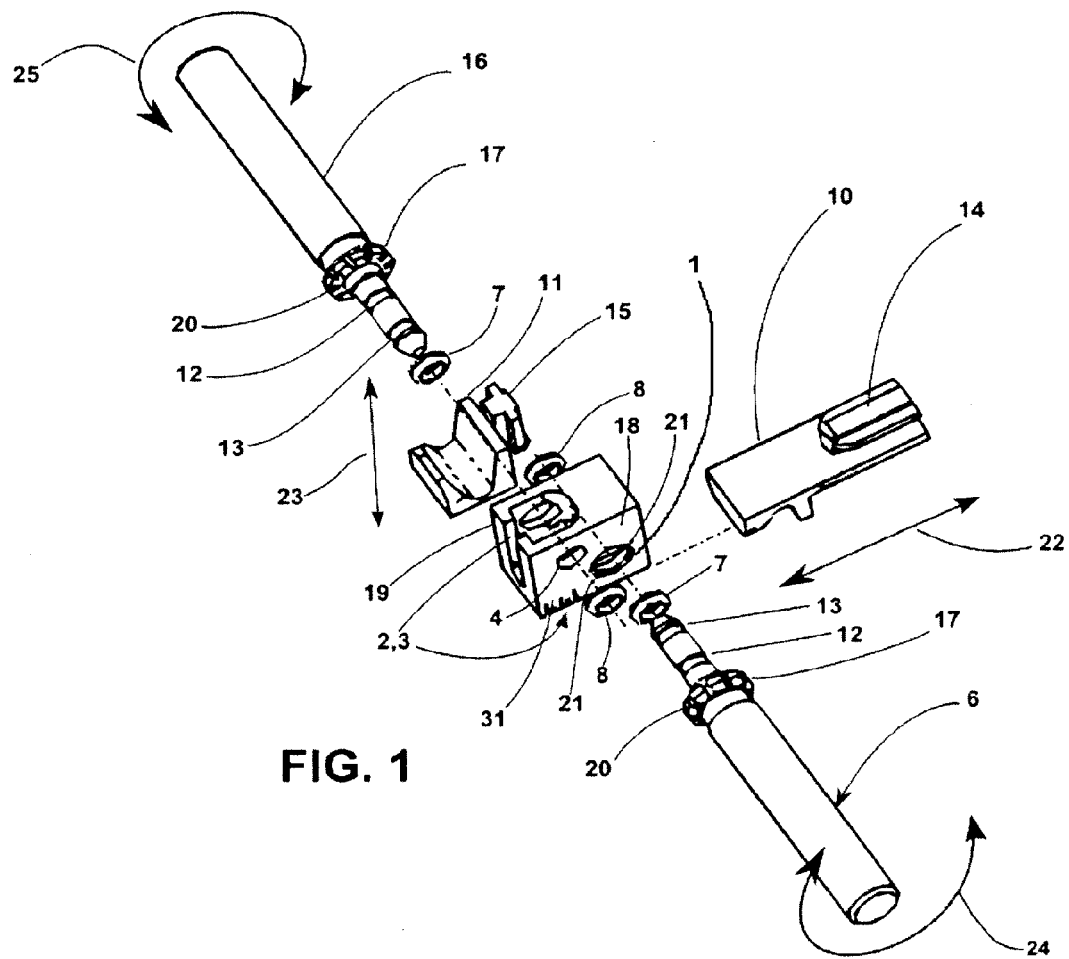
FIG. 1 is an exploded view of a device according to the invention without the mouthpiece or bite register.
Figure 2:
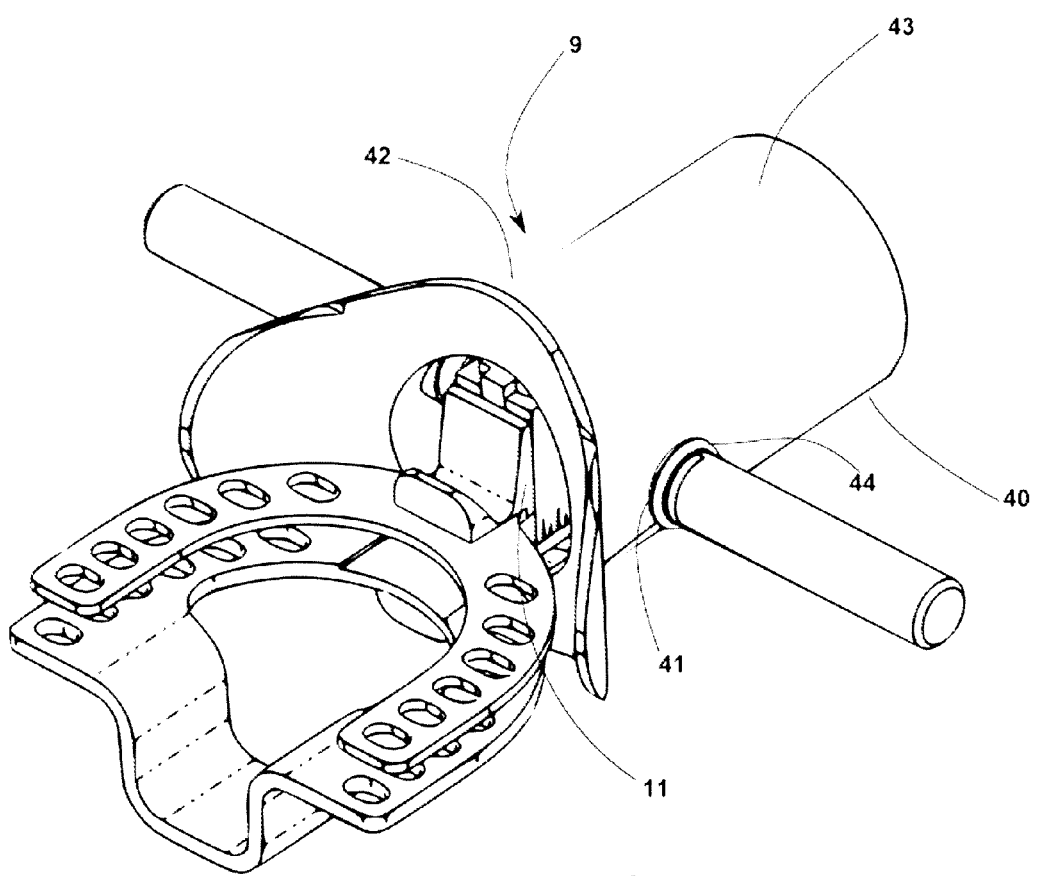
FIG. 2 is a perspective view of the manipulator assembly in its entirety with mouthpiece.
Figure 3:
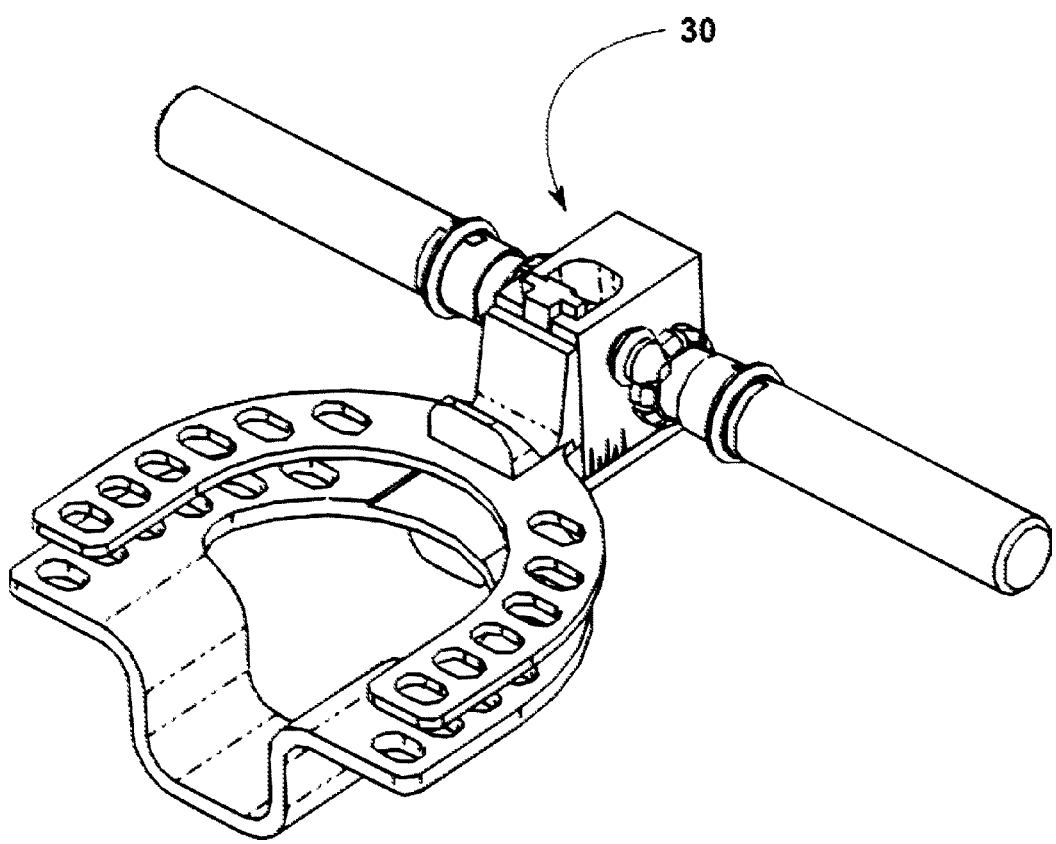
FIG. 3 is a perspective view of the manipulator with bite registers and without the mouthpiece.
Figure 4:
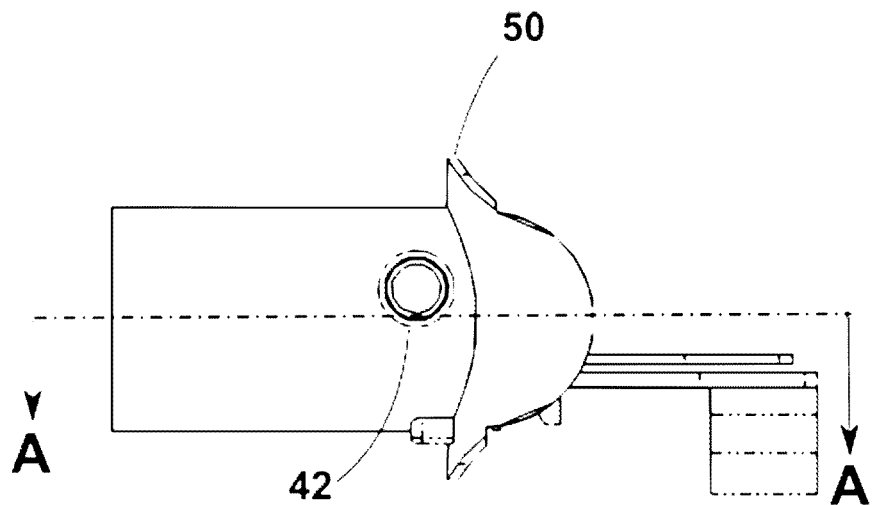
FIG. 4 is a left side view of a device according to the invention.
Figure 5:
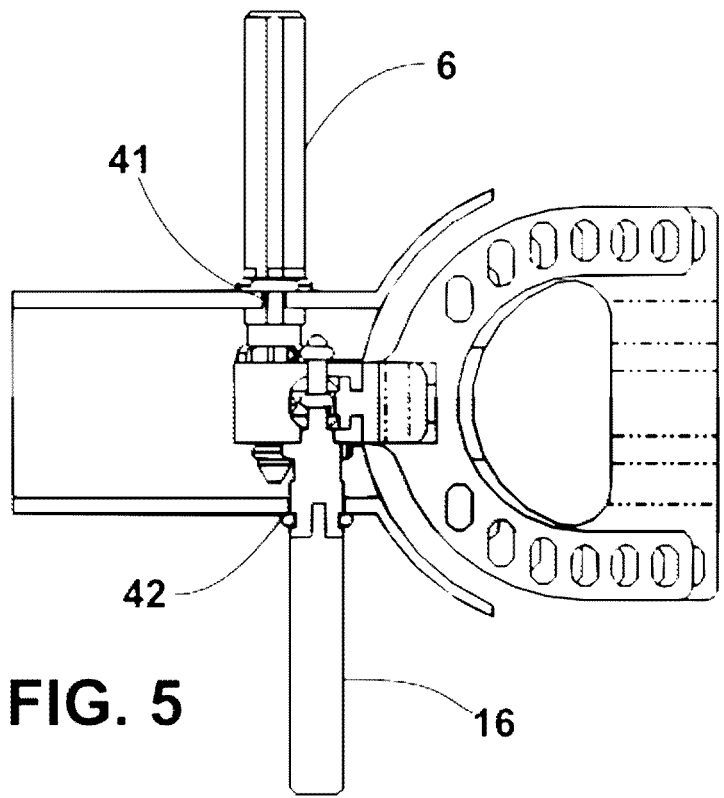
FIG. 5 is a cross sectional view A-A of FIG. 4.

With reference now to FIGS. 1, 2, and 3, arrow 9 shows the overall mandibular manipulator as a self-contained unit for measurement in the anteroposterior and vertical movements of a patient's mandible in relation to the maxilla. The manipulator assembly begins with a frame 1 having slots 2, 3 and aligned holes 4, 5. Pinions 6, 16 are assembled through the holes while adding O-rings 7, 8. In this embodiment, lower incisor pull 10 and upper incisor pull 11 engage and are received by slots 2, 3 and slide in directions shown by arrows 22, 23, respectively.

O-rings 7, 8 serve different functions. O-ring 7 seats on groove 12 and is squeeze against surface 14 and 15 of incisor pulls 10 and 11, respectively. When pinion 6 or 16 are rotated in directions 24 or 25, there is a translation of rotational to linear motion by the friction of O-ring 9 against the incisor pulls 10 and 11, respectively. A small rack and pinion gear set could also take the place of O-ring 7 and surfaces 14, 15 to create a means for the translation of motion. The rack and pinion gear sets 77, 78 are utilized in the embodiment described in FIGS. 16 through 21. O-rings 8 or another ring of resilient form are used to retain pinions 6, 16 within the frame 1 when seated in groove 13. Additionally, O-ring 8 creates an axial bias to the pinions 6, 16. This bias action is used to pull the pinions' 6, 16 flange 17 toward the frame side 18, 19 (19 is the surface opposite 18). Radial slots 20 equally spaced around flange 17 engage protrusions 21 (typical to opposite side of frame for aligned hole 4) to create a soft detent. This detent creates a tactile feedback when the pinion 6 is rotated by hand to offer the operator a measurement of how far incisor pulls 10, 11 have moved relative to rotation shown by arrows 24, 25. A dial or other visual indicator rigidly part of pinion 6, 16 could also be used to indicate distance traveled by incisor pulls 10, 11. Gradation indicators 31 shown in FIG. 1 on frame 1 are used to clearly indicate travel of the pull 10.

In more detail now to FIGS. 2 and 3, the assembled mechanism of FIG. 1, now shown with the bite plate pulls, and shown in FIG. 3 by arrow 30 is assembled within Mouthpiece 40. Holes 41 and 42 provide a fit that is tight enough around pinions 6, 16 to create an acoustic seal. The round cylindrical tube 43 of mouthpiece 40 creates an airway and can be attached to a medical instrument, for instance, an acoustic oral pharyngometer.

Referring now to FIGS. 4, 5, 6, 7, and 15, the mouthpiece 40 is made of resilient material and fits into a patient's mouth similar to a snorkel mouthpiece. Surface of Flange 50 sets within the inner surface of a patient's lips while the incisor pulls 10, 11 engage the patient's front teeth. Upper and lower surfaces of bites 51, 52 are contacted by the patient's molars and incisor teeth. Bites 51, 52 feature through holes 53, 54 provided to hold bite registration paste that would be injected into these areas by a physician or dentist. Tongue depressor 54 formed on bite 51 is used to keep the patient's tongue from interfering with the medical measurement. Tongue depressor 54 is shown also in FIG. 15.

In more detail now to FIG. 8, a perspective view of pinion 6, 16 is shown for communicating in more detail. Conical surface 55 is a feature of the pinion to allow the O-rings 7, 8 to be assembled more easily into grooves 12, 13. Cylindrical surface 56 can have various surface textures applied. One embodiment would be a straight or diamond knurl pattern for instance so as to provide an improved finger grip to the pinion. In yet another embodiment, a soft, resilient tubing such as silicone or latex could slip over surface 56 for the same purpose of providing an improved grip. Cylindrical surface 56 could also be attached to a small servo motor mechanism to drive pinion 6, 16 with a feedback surface to the medical instrument being used. In this way, the entire medical measurement is computer driven and the mandible position is optimized.

Figure 9:
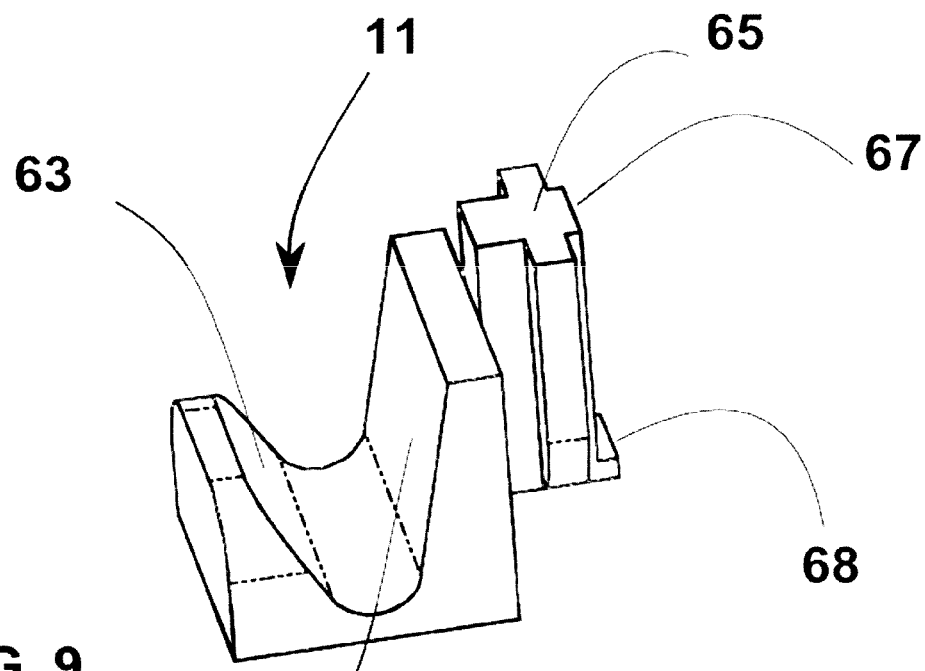
FIG. 9 is a perspective view of the upper incisor pull.
Figure 10:
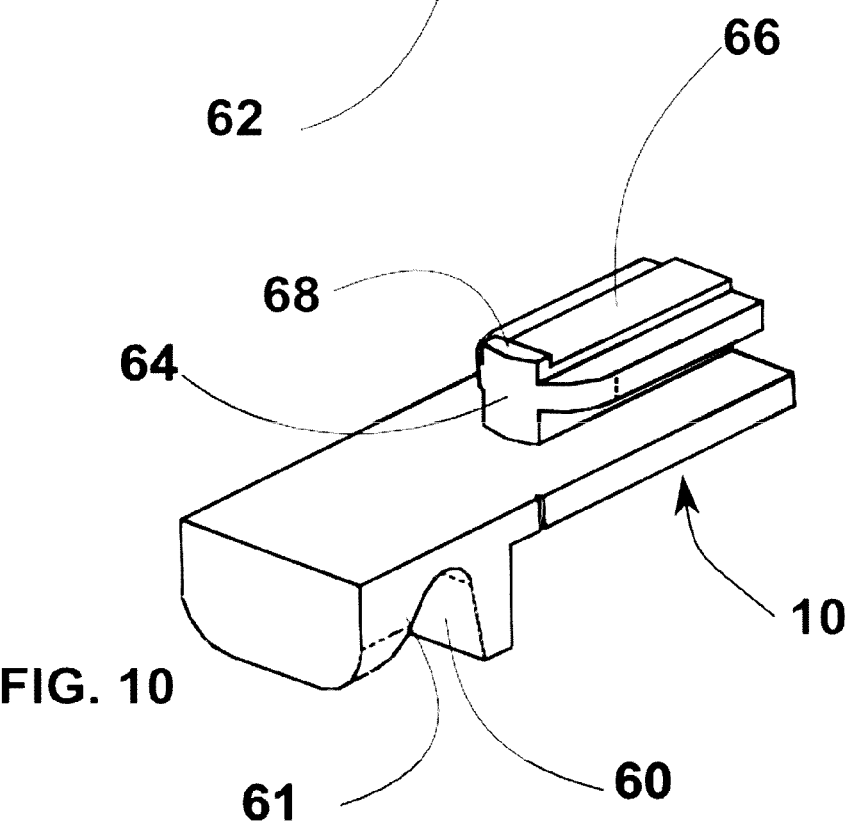
FIG. 10 is a perspective view of the lower incisor pull.
Figure 11:
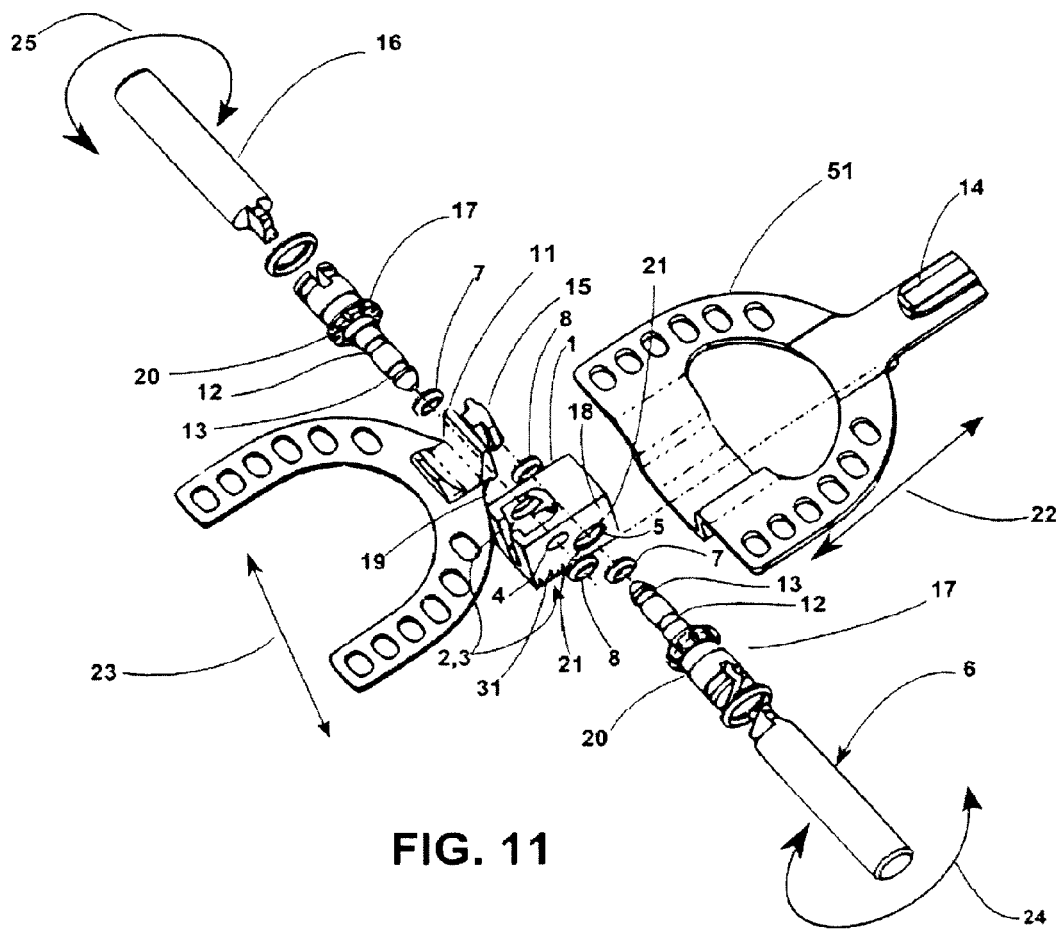
FIG. 11 is an exploded view of a device according to the invention without the mouthpiece while including an integrated bite register.

In more detail now to FIGS. 9 and 10, are the upper incisor pull 11 and lower incisor pull 10, respectively. Both incisor pulls 10, 11 use similar angled walls 61, 62, 63, and 64 to engage and receive the patient's incisors. In another embodiment, these walls could be rounded and reshaped to engage more of the patient's upper and lower teeth surfaces. Both incisor pulls 10 and 11 have similar sliding "T" shaped slides 64 and 65. These guides self-capture in slots 2, 3 of the frame 1. While this is one embodiment of a captured sliding guide, another example would be a dovetail or some similar mechanical capturing slide mechanism. Incisor pull 10, 11 also feature protruding surfaces 66 and 67 which allow for both adjustment of the O-ring 7 pressure and provide a roughened surface to provide more friction to the O-ring 7. In another embodiment, surfaces 66 and 67 could be gear rack teeth, which would engage mating gear teeth on pinion 6, 16 in place of O-ring 7. Other types of translation from rotational to linear motion could be used in this application.

Figure 12:
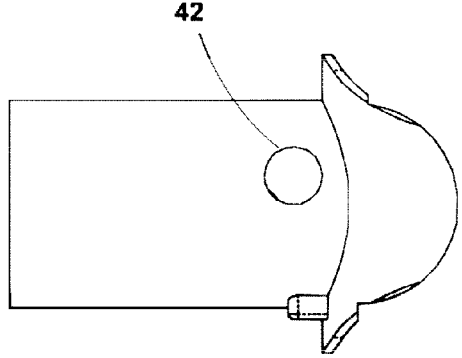
FIG. 12 is a side view of the mouthpiece.
Figure 13:
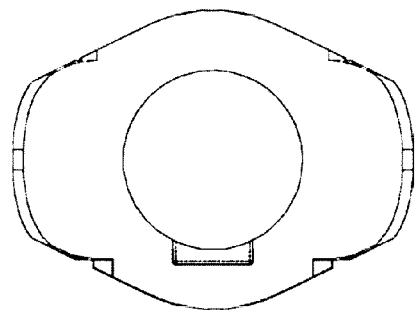
FIG. 13 is a rear view of the mouthpiece.
Figure 14:
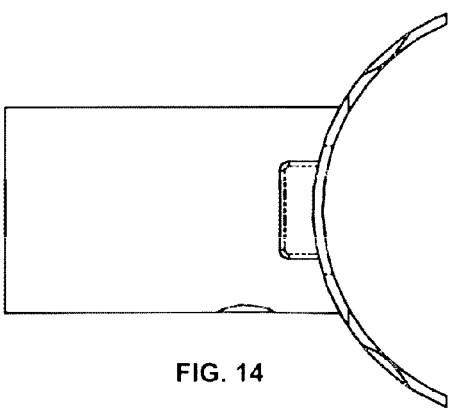
FIG. 14 is a bottom view of the mouthpiece.

FIGS. 12, 13, and 14 are orthographic views of the mouthpiece 9.

Figure 15:
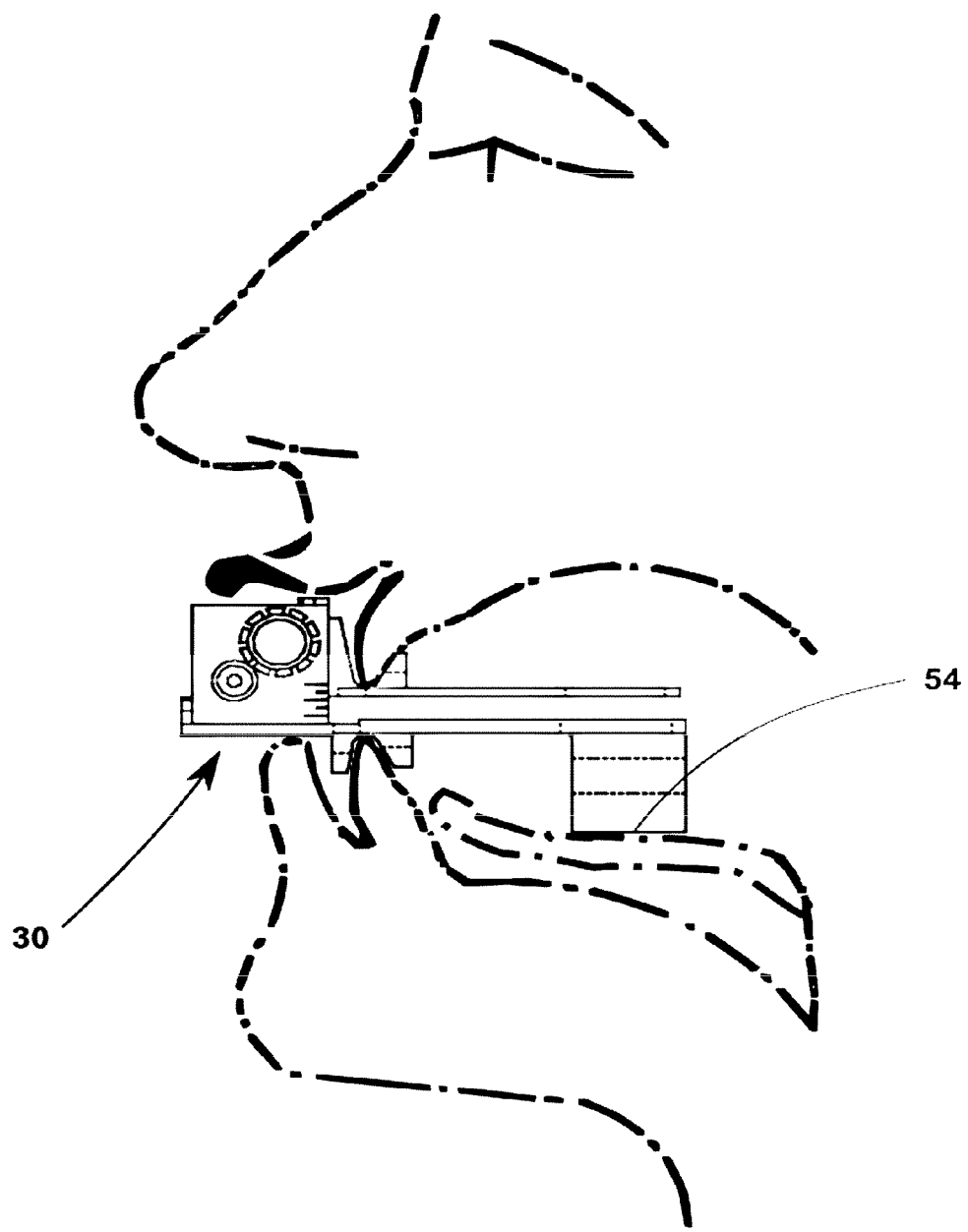
FIG. 15 is a cross-sectional side view of the lateral maxilla and mandible with the invention that includes the integrated bite register.
Figure 16:
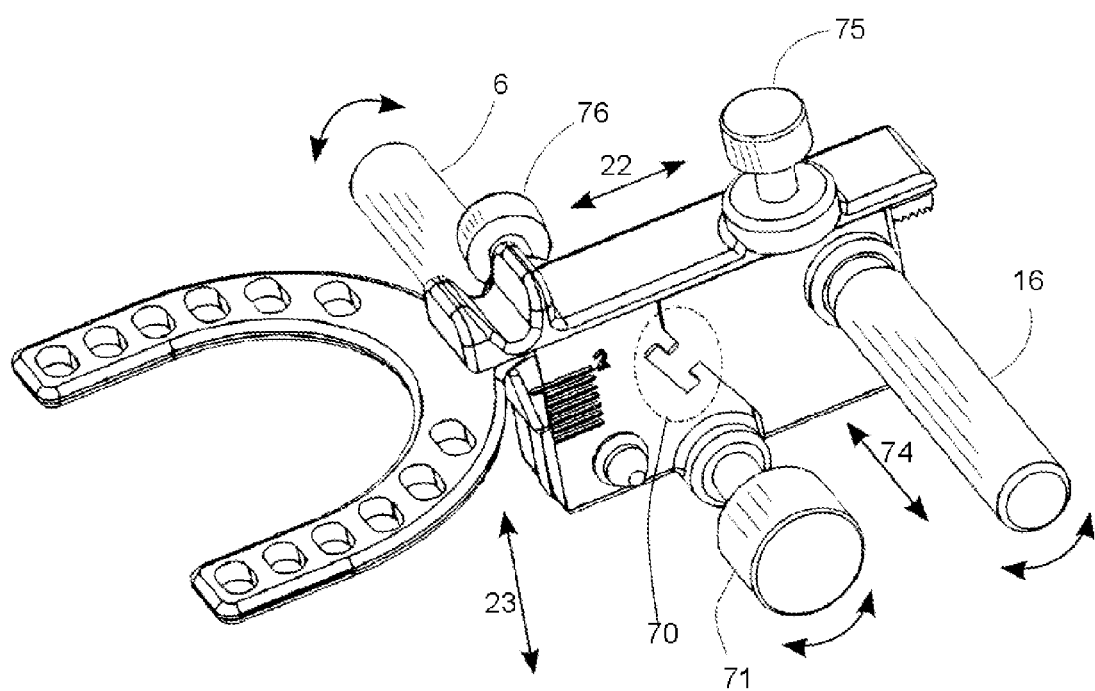
FIG. 16 is a perspective view of the embodiment which allows for the measurement of the mandible relative to the maxilla in three dimensions.

Another embodiment of the invention allows for the measurement of the mandible relative to the maxilla in three dimensions. FIG. 16 shows a detailed perspective view in which an additional sliding joint 70 is added to the instrument to provide for the patient's mandible measurement in the sagittal direction. This embodiment would be applied to the patient as described in FIG. 15. In this instance, frame 1 is now two parts 71, 72 while each carries the slots 2, 3 and corresponding aligned holes 4, 5, respectively. Frame parts 71, 72 interact and attach to one another through joint 70. Joint 70 forms the sagittal axis of movement. The sagittal movement, described by arrow 74, is accomplished by adjusting element 73. Incisor pulls 10, 11 with incisor pull 11 having an arched bite configuration as described earlier, and move in the same manner as described per FIG. 1.

Figure 17:
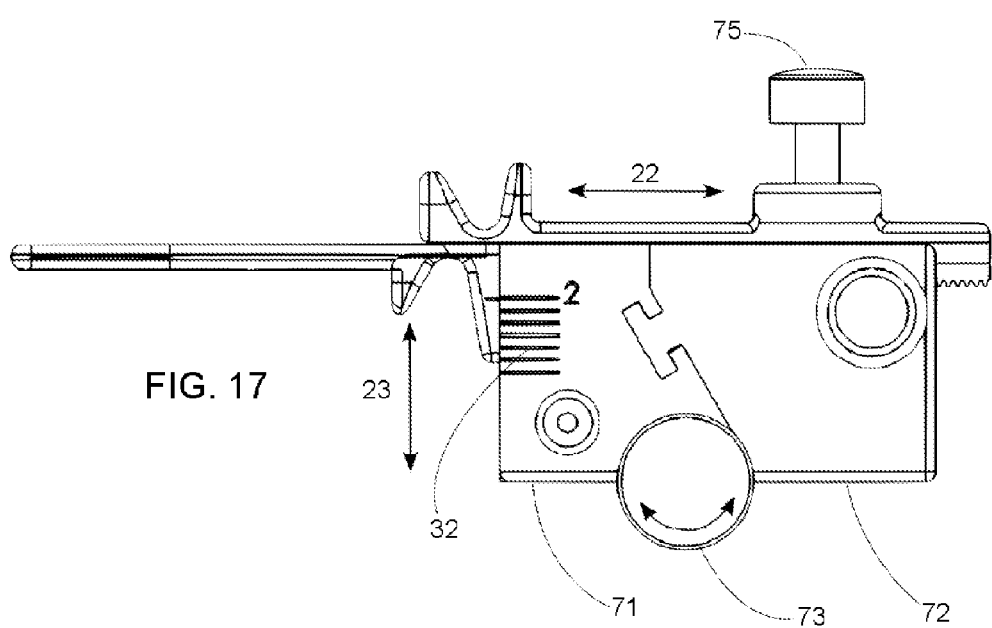
FIG. 17 is a right view of the embodiment of FIG. 16.
Figure 19:
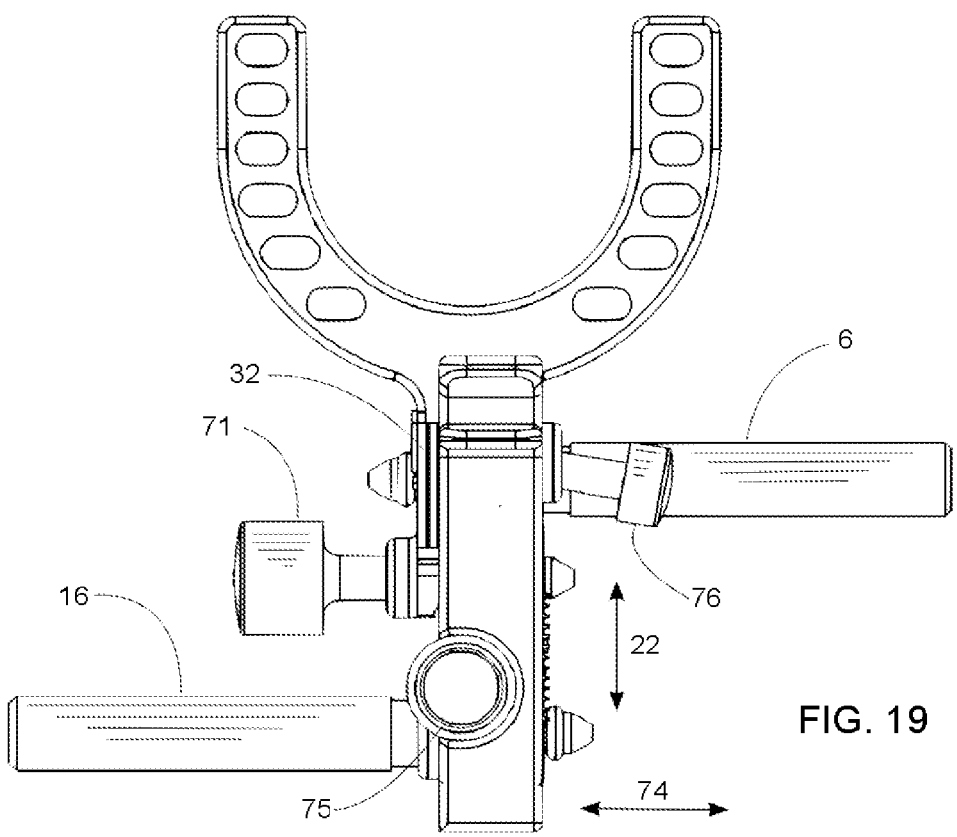
FIG. 19 is a top view of the embodiment of FIG. 16.
Figure 20:
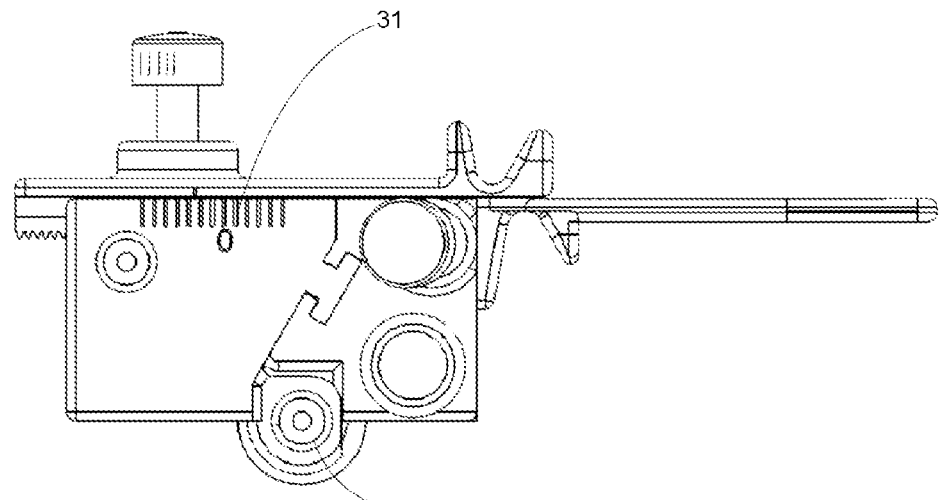
FIG. 20 is a left side view of the embodiment of FIG. 16.

FIGS. 17, 19, and 20 show the gradation indicators 31, 32, and 33, accurately describing the movement for each axis of the instrument. Once the instrument has been adjusted for the ideal position for the patient, motions 22 and 23 are locked using fixation members 75, 76. FIG. 17 shows gradation indicators 32 with the normal occlusion starting point of 2 mm represented by the numeral 2 in the figure. FIG. 20 shows the gradation indicators 31 with the numeral 0 representing the normal occlusion location. In some embodiments, the numeral 0 on the mandibular manipulator may be positioned to indicate a point of zero occlusion. In other words, when incisor pull 10 (FIG. 1) is positioned at numeral 0 of the gradation indicators 31, the incisor pulls 10, 11 of the mandibular manipulator may be configured to align the upper and lower incisor teeth of the subject. For example, when incisor pull 10 (FIG. 1) is positioned at numeral 0 of the gradation indicators 31, the upper and lower incisor teeth of the subject may be substantially vertically aligned in an edge-to-edge relationship as shown in FIG. 15).

Figure 18:
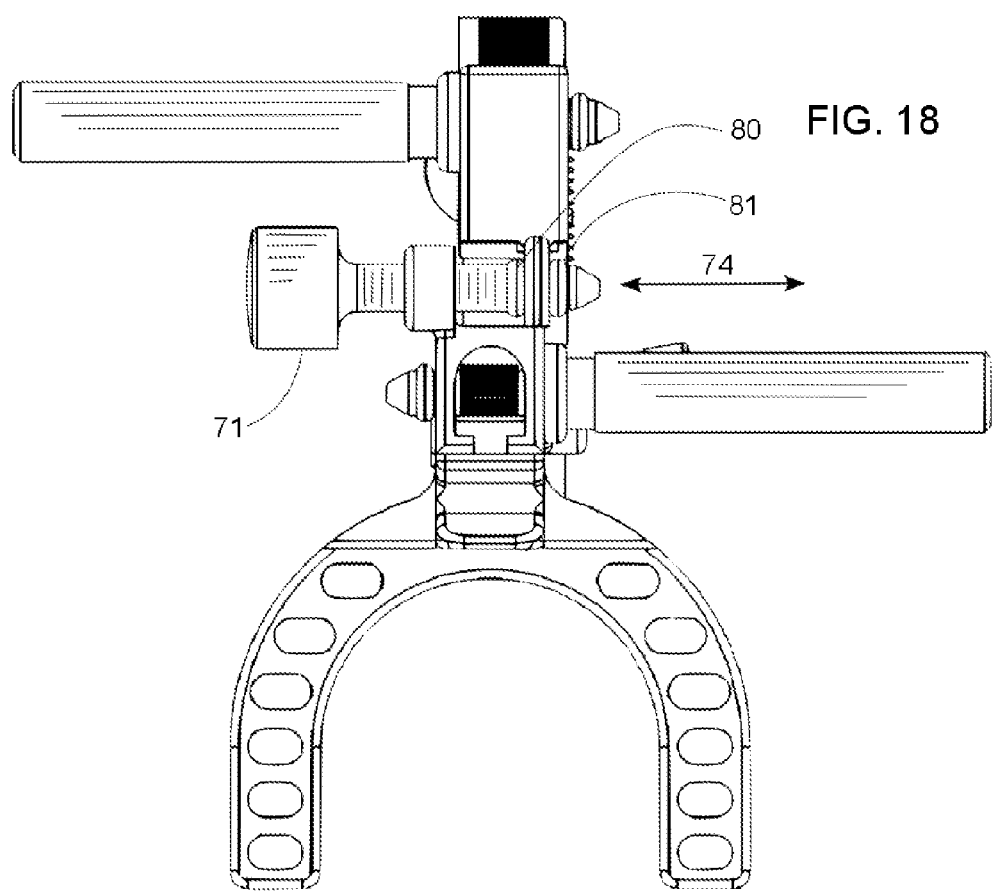
FIG. 18 is a bottom view of FIG. 17.

Referring to FIG. 18, the sagittal slide 70 allows frame blocks 71, 72 to move relative to one another by adjusting screw 73. Adjusting screw 73 is threaded into hole 78 in frame block 71 and then attached to frame block 72 through hole 79 and retained with two resilient rings or O-rings 80, 81.

Figure 21:
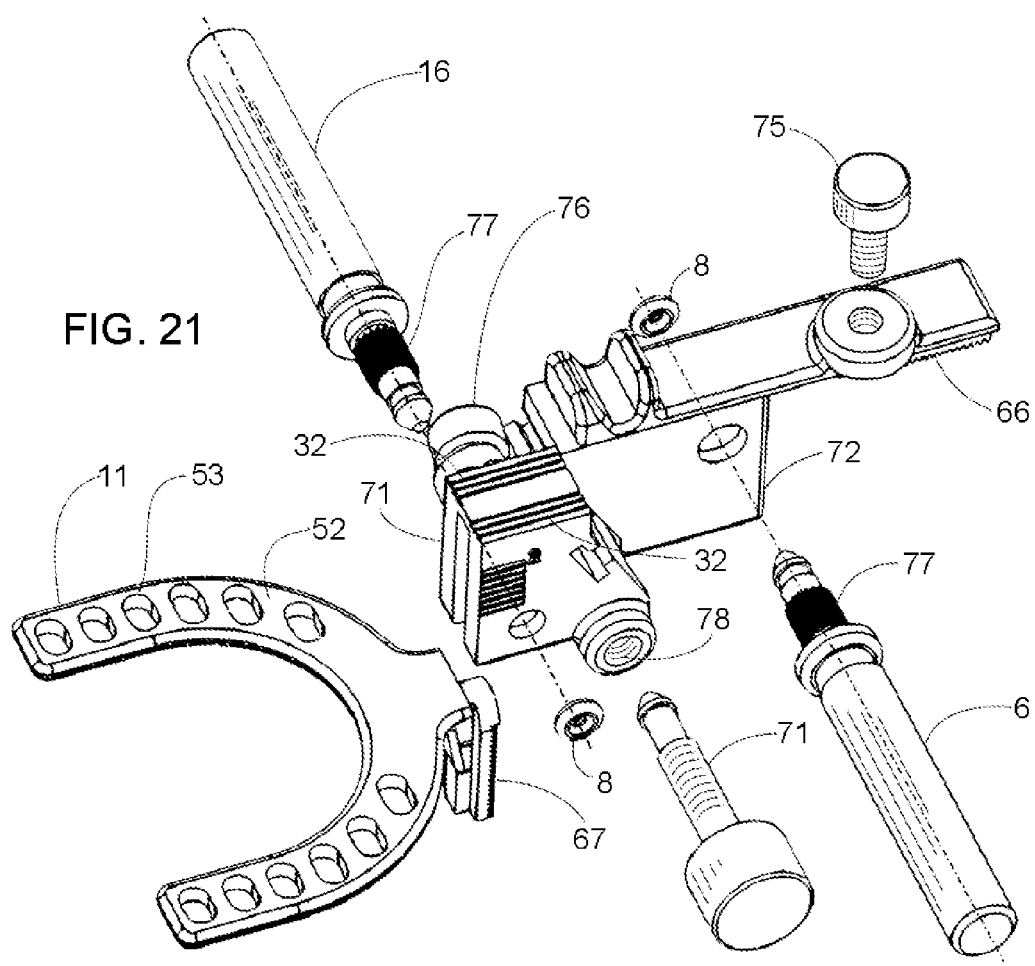
FIG. 21 is an exploded view of the embodiment of FIG. 16.

FIG. 21 shows the exploded view of the mandibular manipulator for taking a patient's measurement in three orthogonal axes. As described earlier, incisor pull 11 shown with the arch bite, can have bite paste applied to surface 52 and holes 53 by a physician or dentist or other health care worker to create a precisely located bite registration.

Figure 22:
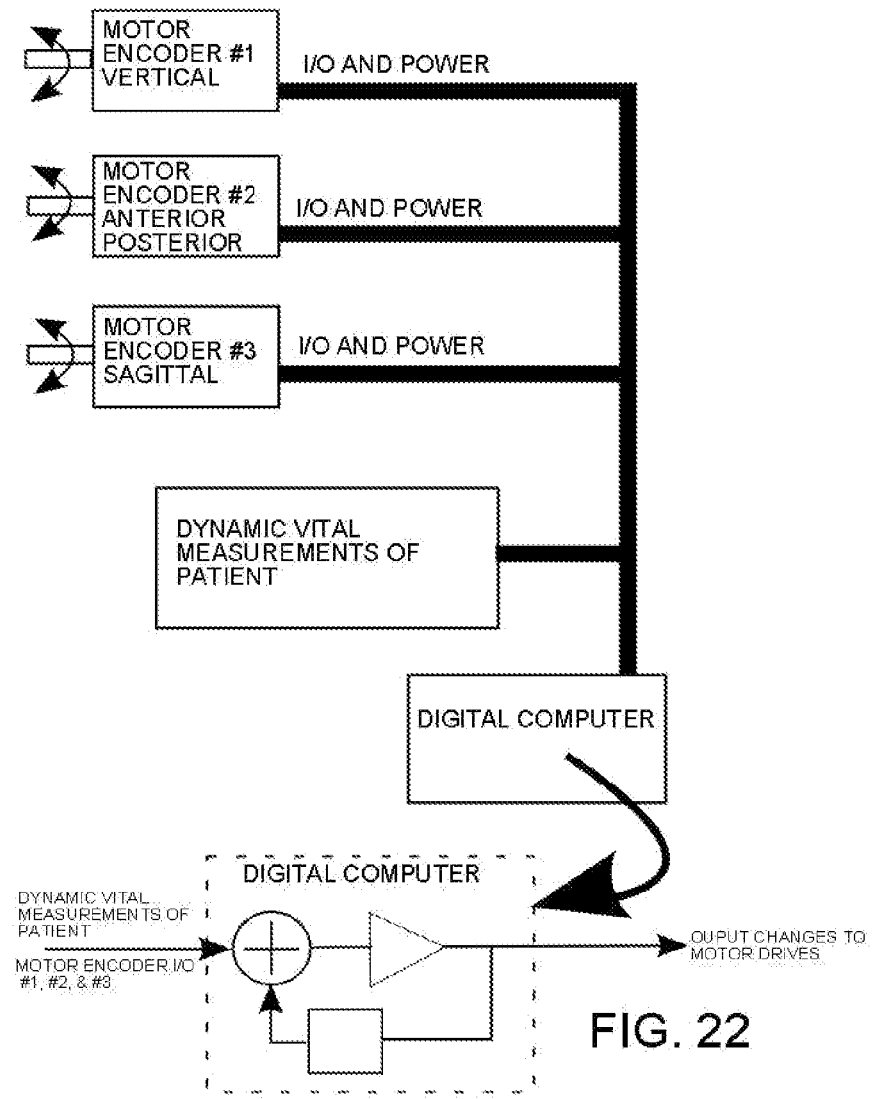
FIG. 22 is a block diagram of the manipulator driven by digital computer.

FIG. 22 shows an automated means of operating the invention by a personal computer and software. Real-time physical information of the patient is mixed with encoder information from the mandibular manipulators motor drives. These inputs are then analyzed by digital computer software to optimize the motor positioning creating the ideal mandible position for the patient. The positions can then be recorded and used as part of a bite registration method or to indicate a prescribed outcome for the patient by the physician or dentist.

Figure 23:
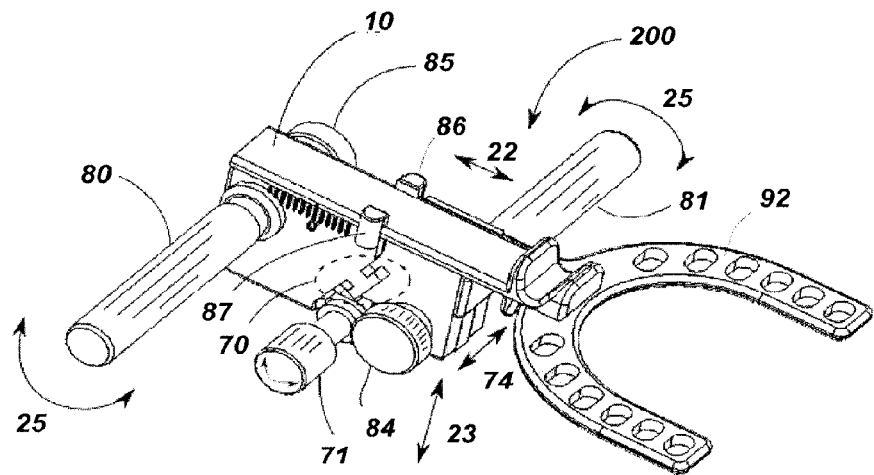
FIG. 23 is a perspective view of the embodiment with enhanced locking mechanism, which allows for the measurement of the mandible relative to the maxilla in three dimensions.
Figure 24:
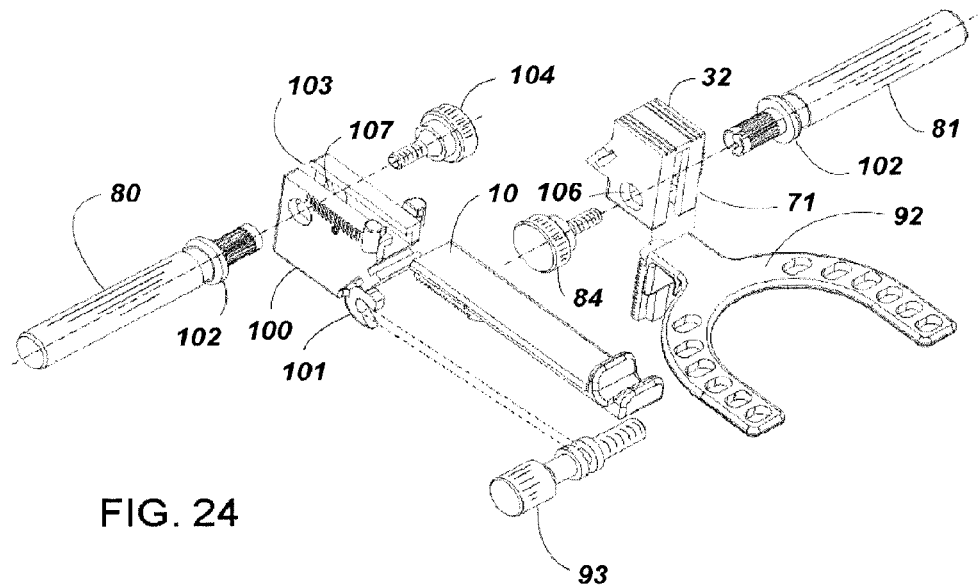
FIG. 24 is an exploded view of the embodiment of FIG. 23.

A further embodiment of the invention 200 is shown with reference now to FIG. 23 and exploded view FIG. 24. A linear motion is produced in incisor pull 10 and 92 when pinions 80 and 81 are rotated as shown by arrows 25. The mechanical interaction between the pinions, 80, 81 and 10, 92, respectively is by gear teeth but other friction type of communication between these parts could also be used. The sagittal movement 74 of block 32 and upper block 100 are created by sagittal screw 93 when it is rotated. The T-slide 70 provides the constrained guidance to maintain a linear motion 74 between block 32 and upper block 100.

Figure 30:
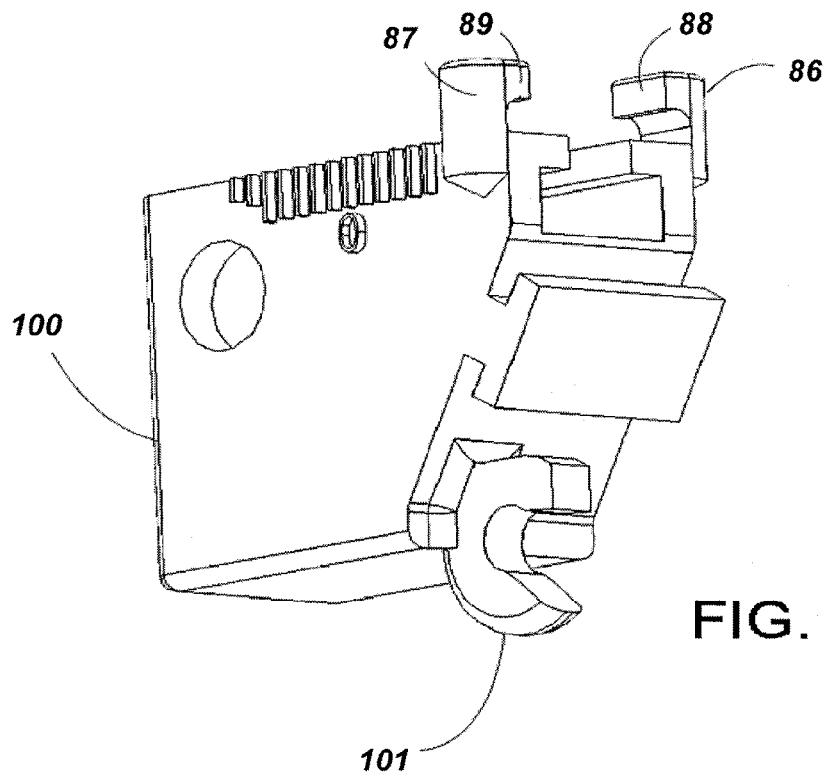
FIG. 30 is a perspective view of the upper block 100.
Figure 31:
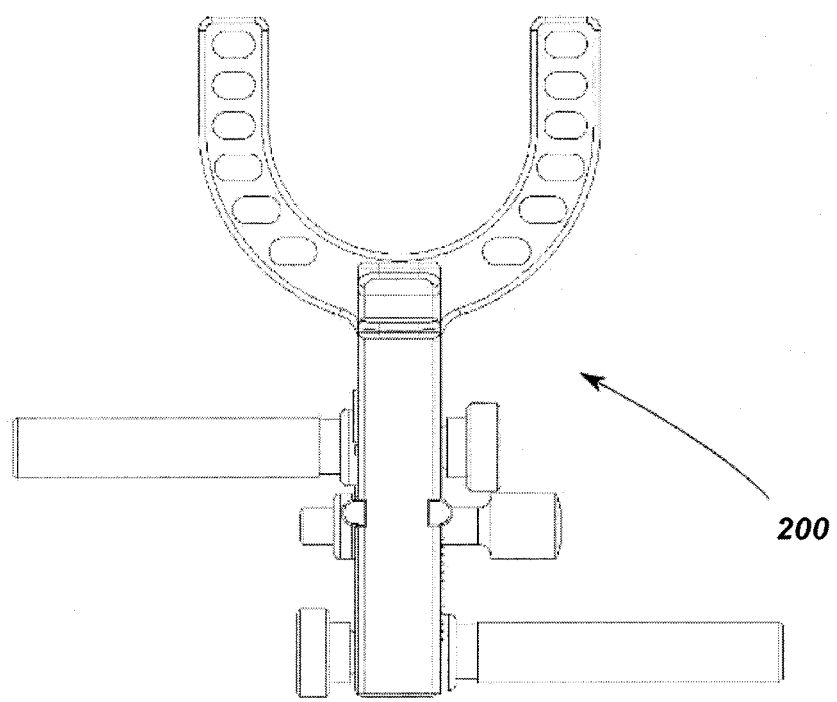
FIG. 31 is a top view of the embodiment of FIG. 23.

Referring now to FIG. 30 are the posts 86, 87, which form a channel with surfaces 88, 89 and provide a supported and captured travel to upper incisor pull 10. Posts and surfaces 86, 87 and 88, 89 prevent upper incisor pull 10 from yawing or pitching up when pinion 80 is rotated.

Figure 27:
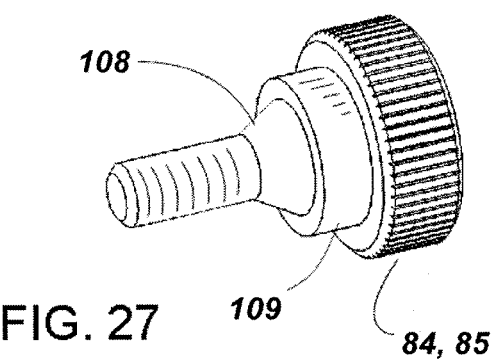
FIG. 27 is a perspective view of the locking screw 84, 85.
Figure 28:
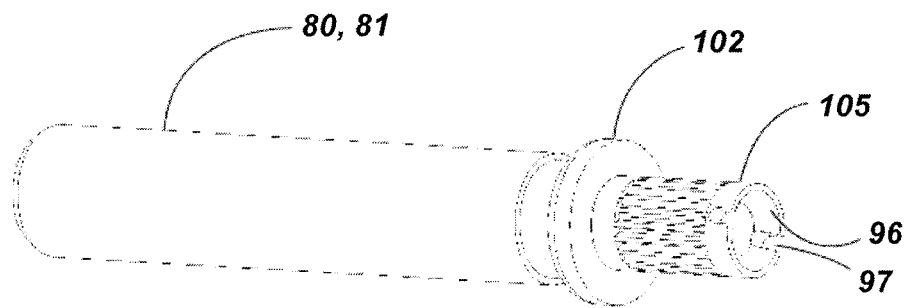
FIG. 28 is a perspective view of the pinion 80, 81.

Referring now to the exploded view of FIG. 24 and FIGS. 27, 28, locking screws 84, 85 are indicated and thread into pinions 80, 81, respectively. A locking stop function is created by 84, 85 in two ways. First, shoulder 109 of FIG. 27 and pinion flanges 101, 102 are forced together through the threads of the locking screw 104 thus also squeezing slot 103 to clamp the slide of upper incisor pull 10. Secondly, there is a truncated cone shape 109 feature on locking screw 84, 85 that contacts an inverted cone shape 96 internal to pinions 80, 81. The thread of screw 84, 85 forces the bearing surface 105 outward by relief of slot 97 and stops the motion of pinions 80, 81 through friction communication of surfaces 105 and aperture surfaces 106, 107. Only a pair of slots 97 are shown but other multiple slots could also be added to provide more bias to the braking surface 105.

Figure 25:
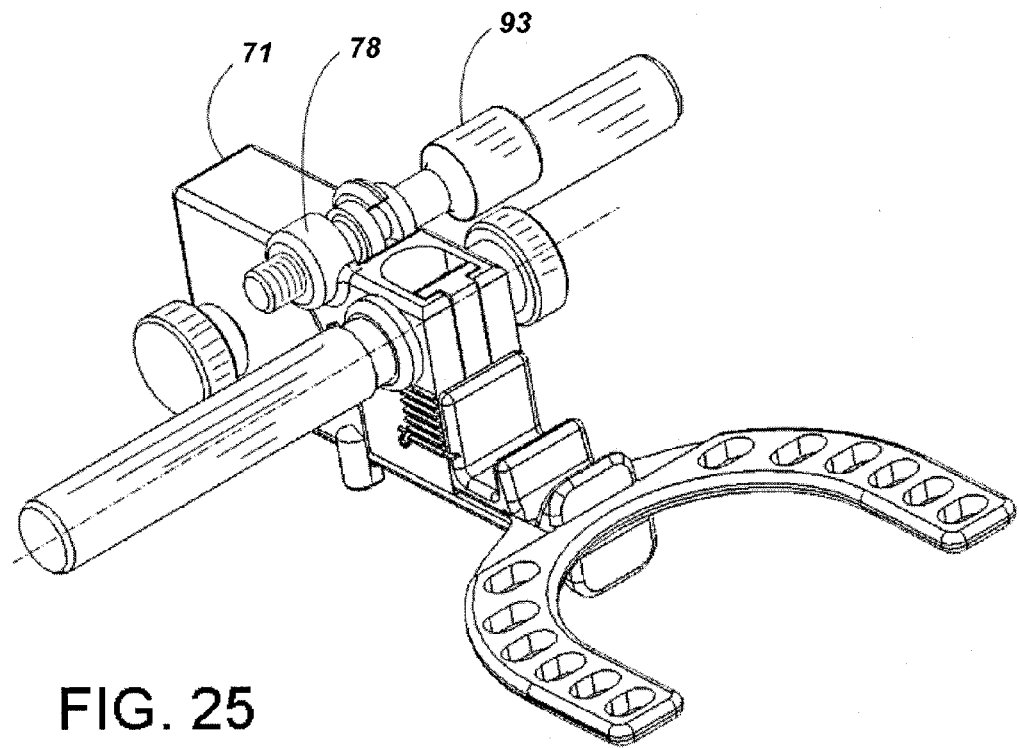
FIG. 25 is a bottom perspective view of the embodiment of FIG. 23.
Figure 29:
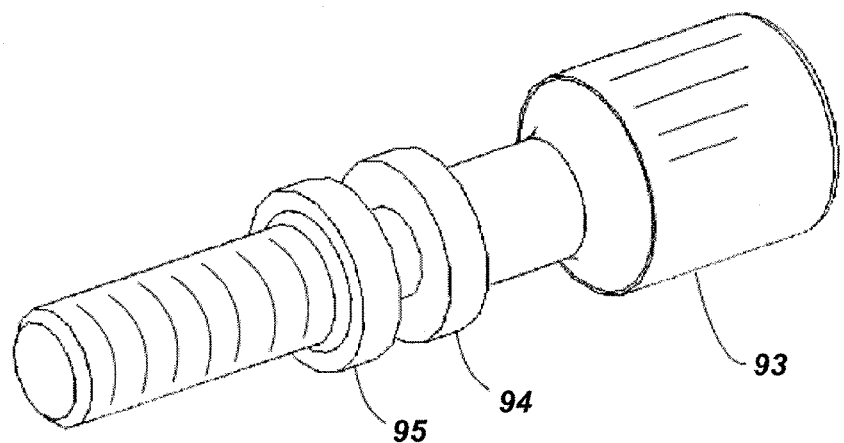
FIG. 29 is a perspective view of the sagittal screw 93.

Referring to FIGS. 24, 29, and 30, sagittal screw 93 is retained in block 100 by an over-center snapping feature fork 101. Fork 101 is receives the sagittal screw 93 between flanges 94, 95. The communication between block 100 and screw 93 is such that the screw can rotate and yet maintain position relative to Block 100. Referring to FIG. 25, a mating threaded boss 78 on block 71 receives the threaded portion of screw 93 and provides the precise sagittal motion 74 required of the invention.

Figure 26:
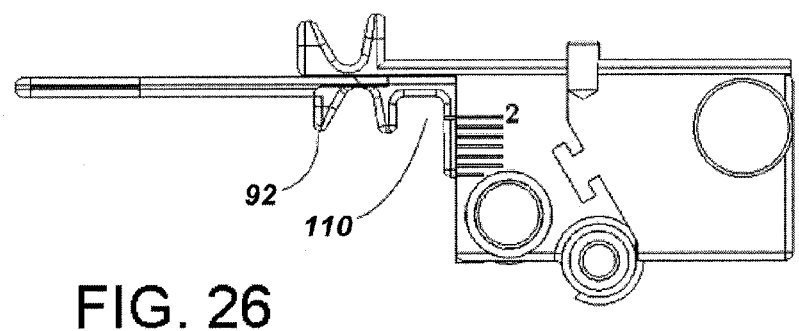
FIG. 26 is a left hand view of the embodiment of FIG. 23.

Referring to FIG. 26, a space 110 is left between the incisor groove of lower pull 92 to allow space for a patient's lip.

As previously described, the current state of the art for manipulating a patient's mandible includes the well-known GEORGE GAUGE™. The GEORGE GAUGE™ allows for the movement of the lower mandible only in the anteroposterior axis and minimal vertical change, whereas the instant device measures the vertical distance of the mandible as well as the anteroposterior distance of the mandible, and the relative sagittal location, all relative to the maxilla. However, while Leal and Halstrom (see, for example, U.S. Pat. No. 7,448,388) both utilize a means of using two bite register plates, neither can be adjusted in real time using any diagnostic instruments.

In a particular embodiment, the invention includes a mandibular manipulator for manipulating a patient's jaw in a precise way, the mandibular manipulator having a connecting frame 18 comprising a piece with apertures and slots 2, 3 therein to allow first and second sliding incisor pulls (or cradles 10, 11) and first and second rotational members or knobs 6, 16 associated with each of the first and second sliding incisor pulls, respectively, to be moved independently of one another with respect to the connecting frame in order to manipulate the patient's jaw in a precise way. Each of the sliding incisor pulls has an associatable sliding member for interaction with the connecting frame at a slot and a cradle member associated with the sliding incisor pulls shaped to engage the patient's teeth and/or gums for manipulation of the jaw. Further, each rotational member is associated with the connecting frame at an aperture, and comprises a member or portion in physical contact with the associated sliding incisor pull at an interface therewith so as to change rotational motion of the rotational member to linear motion of the sliding incisor pulls and thus adjust each the respective sliding incisor pull with respect to the connecting frame and the patient's jaw and thus manipulate the jaw in longitudinal and vertical manners with respect to the patient's mouth; and horizontal and vertical gradation indicators (or markings), associated with the connecting frame, for measuring relative movement of the sliding incisor pulls with respect to the connecting frame caused by rotating the first and second rotational members and utilizing the mandibular manipulator.

Such a device may further have a mouthpiece having a cylindrical end 43 thereon that provides an air passageway for the patient and a closing cap at the air passageway that can form an acoustic seal, the mouthpiece having apertures 41, 42 therethrough through which the first and second rotational members extend therefrom in an acoustically sealed manner around the rotational members; the resilient mouthpiece further having bites 51, 52 with apertures 53, 54 to receive bite registration paste.

In developing the disclosed device, a period of methodical process was undertaken with varying instruments. The first instrument was a telescoping circular tube within a circular tube with similar shaped incisor pulls that are in the described invention. This early instrument connected the upper incisor pull to a rotating cam and the center tube provided a means of rotation for providing the vertical motion (see FIG. 1). Two drawbacks of this first instrument were that it could not be used in real time with a pharyngometer mouthpiece and the rotation of the upper incisor pull to create the vertical motion also created a side load that prevented the mandible and maxilla to stay central to one another. The anteroposterior manipulation of the mandible proved successful with this first instrument.

Drawbacks to a second instrument were a slipping fit problem between the pinch wheels and incisor pulls for translating rotational motion to linear motion. The pinion handles were also too long preventing its installation in the snorkel like mouthpiece after it was assembled. The incisor pulls also did not have a stop feature allowing them to come free of the frame. There were no graduated markings for visually reading the position of the incisor pulls nor was there a centering groove in the frame for positioning the instrument relative to the upper incisors.

As disclosed herein, the relative position of the incisor pulls to the O-ring pinch wheels was closed substantially to provide a near non-slip action as the pinion changes rotational motion to linear motion. Small mechanical features were added to the incisor pulls to prevent them from coming free of the frame once the pinions were assembled to the frame. The pinions were shortened in length and provided with a feature to allow an extension handle to be added. This allows the instrument to be installed within the snorkel mouthpiece and then have the extension pieces added post assembly.

The snorkel like mouthpiece also went through a development process. When the instrument's lower bite plate incorporates a tongue depressor, the mouthpiece can be simplified. The internal cylindrical diameter that holds the manipulator assembly has to be of the same internal diameter as the acoustic pharyngometer's acoustic waveguide, to allow for accurate measurements by the pharyngometer. Although the relative distances from the teeth to the pharyngeal remain constant, the overall distances from the end of the acoustic waveguide are shifted the additional distance of the invention's lengthened mouthpiece tube versus the standard length mouthpiece that is provided by the pharyngometer's manufacturer. A relief is provided in the lower portion of the mouthpiece tube to allow the lower incisor pull to travel into the tube without interference. This relief provides a proper extension of the lower incisor pull.

The upper incisor pull allows extensions of about from 4 mm to about 7 mm from its neutral starting position while the lower incisor pull must allow extensions of from about 7 to about 11 mm from its neutral position. These distances are what is preferred by dentists and physicians for the inclusion of most patient's natural maxilla and mandible shapes and positions.

A second problem with the current state of the art is that the motion measured with a George Gauge™ can only be performed in one plane. The invention allows three planes of measurement for both dental and medical practices required of a two- or three-plane measurement. Also, the George Gauge™ cannot be used remotely for real-time measurement. This is in fact due to the need to adjust anterior/posterior position in the same axis as the diagnostic instruments being used. A similar problem is encountered with the instruments by Halstrom or Leal.

This disclosure provides a means of moving and measuring the mandible position in real time as the patient is undergoing diagnostic procedures. The manipulation can be done by hand within the medical procedure for monitoring real-time feedback from diagnostic instruments or the manipulation can be motor driven with computer feedback to obtain the ideal position. The manipulation of the mandible relative to the maxilla by the invention, allows for real-time measurements to take place with repeatable precision thus decreasing diagnoses time while accurately quantifying the position of the upper and lower bite of the teeth. In this way, a dental appliance can be accurately built from the dental articulator as a result of the procedure. It can also allow the physician or dentist to prescribe another method to reduce the episodes of sleep apnea.

Those readily knowledgeable in the art could manufacture the pieces of the invention by methods that would include machining or molding. The materials that could be utilized to create the parts of the invention may include metals, polycarbonate, nylon, polypropylene, and delrin.

What is claimed is:

1. A mandibular manipulator for manipulating a patient's mandible in a precise way, the mandibular manipulator comprising:
a connecting frame comprising:
a first sliding incisor pull;
a second sliding incisor pull;
a first rotational member associated with the first sliding incisor pull;
a second rotational member associated with the second sliding incisor pull, the connecting frame enabling the first sliding incisor pull and the second sliding incisor pull to be moved independently of one another with respect to the connecting frame by the first rotational member and the second rotational member, wherein each of the sliding incisor pulls comprises an associatable sliding member for interaction with the connecting frame at a slot and a cradle member associated with the sliding incisor pulls shaped to engage the patient's teeth and/or gums for manipulation of the mandible, and further wherein each rotational member is associated with the connecting frame at an aperture, and comprises a member or portion in physical contact with the associated sliding incisor pull at an interface therewith so as to change rotational motion of the rotational member to linear motion of the sliding incisor pulls and thus adjust each respective sliding incisor pull with respect to the connecting frame and the patient's mandible and thus manipulate the mandible in a longitudinal and vertical manner with respect to the patient's mouth; and
a third rotational member for converting rotational motion of the third rotational member to linear motion between a first portion of the frame and a second portion of the frame, wherein movement of the first portion of the frame relative to the second portion of the frame moves the first sliding incisor pull relative to the second sliding incisor pull in order to manipulate the subject's mandible in a third lateral direction; and
horizontal and vertical gradation indicators, associated with the connecting frame, for measuring relative movement of the sliding incisor pulls with respect to the connecting frame caused by rotating the first and second rotational members and utilizing the mandibular manipulator.

2. The mandibular manipulator of claim 1, wherein the third rotational member provides for sagittal movement of the mandible.

3. The mandibular manipulator of claim 2, further comprising sagittal gradation indicators for measuring sagittal movement of the mandible caused by manipulating the third rotational member of the mandibular manipulator.

4. The mandibular manipulator of claim 3, wherein the horizontal, vertical, and sagittal gradation indicators are not applied to the first rotational member, second rotational member, or third rotational member.

5. The mandibular manipulator of claim 1, wherein each rotational member has a flange adapted to engage a stationary protruding surface and create a soft detent of the rotation.

6. The mandibular manipulator of claim 1, wherein each rotational member has a slip resistant surface adapted for grabbing.

7. The mandibular manipulator of claim 1, wherein at least one rotational member is threaded for association with a corresponding threaded receptacle in the connecting frame.

8. The mandibular manipulator of claim 1, wherein the sliding member of at least one of the first sliding incisor pull and the second sliding incisor pull has arched plates physically associated therewith, the arched plates having apertures therethrough for receiving bite registration material.

9. The mandibular manipulator of claim 1, wherein at least one rotational member is motorized.

10. The mandibular manipulator of claim 9, wherein the at least one rotational member that is motorized is controlled by computer software.

11. The mandibular manipulator of claim 1, wherein the cradle member of at least one of the first sliding incisor pull and the second sliding incisor pull is spaced from the connecting frame to provide space for the patient's lip.

12. The mandibular manipulator of claim 1, further comprising a mouthpiece having a cylindrical end thereon that provides an air passageway for the patient and a closing cap at the air passageway that can form an acoustic seal, said mouthpiece having apertures therethrough through which the first and second rotational members extend therefrom in an acoustically sealed manner around the rotational members.

13. A mandibular manipulator for manipulating a patient's mandible in a precise way, the mandibular manipulator comprising:
a connecting frame comprising:
a first sliding incisor pull;
a second sliding incisor pull;
a first rotational member associated with the first sliding incisor pull; and
a second rotational member associated with the second sliding incisor pull, the connecting frame enabling the first sliding incisor pull and the second sliding incisor pull to be moved independently of one another with respect to the connecting frame by the first rotational member and the second rotational member, wherein each of the sliding incisor pulls comprises an associatable sliding member for interaction with the connecting frame at a slot and a cradle member associated with the sliding incisor pulls shaped to engage the patient's teeth and/or gums for manipulation of the mandible, and further wherein each rotational member is associated with the connecting frame at an aperture, and comprises a member or portion in physical contact with the associated sliding incisor pull at an interface therewith so as to change rotational motion of the rotational member to linear motion of the sliding incisor pulls and thus adjust each respective sliding incisor pull with respect to the connecting frame and the patient's mandible and thus manipulate the mandible in a longitudinal and vertical manner with respect to the patient's mouth; and
a third rotational member for sagittal movement of the mandible, wherein the third rotational member creating the sagittal movement is held in place by an over-center fork retainer, and wherein the third rotational member is constrained in axial motion by flanges on the third rotational member fitting to each side of the fork.

14. A mandibular manipulator for manipulating a patient's mandible in a precise way, the mandibular manipulator comprising:
a connecting frame comprising:
a first sliding incisor pull;
a second sliding incisor pull;
a first rotational member associated with the first sliding incisor pull; and
a second rotational member associated with the second sliding incisor pull, the connecting frame enabling the first sliding incisor pull and the second sliding incisor pull to be moved independently of one another with respect to the connecting frame by the first rotational member and the second rotational member, wherein each of the sliding incisor pulls comprises an associatable sliding member for interaction with the connecting frame at a slot and a cradle member associated with the sliding incisor pulls shaped to engage the patient's teeth and/or gums for manipulation of the mandible, and further wherein each rotational member is associated with the connecting frame at an aperture, and comprises a member or portion in physical contact with the associated sliding incisor pull at an interface therewith so as to change rotational motion of the rotational member to linear motion of the sliding incisor pulls and thus adjust each respective sliding incisor pull with respect to the connecting frame and the patient's mandible and thus manipulate the mandible in a longitudinal and vertical manner with respect to the patient's mouth, wherein the first and second rotating members creating linear motion of the incisor pulls are locked in placed by a threaded screw with truncated cone to expand the rotating member and grip its bearing surface.

15. A mandibular manipulator for manipulating a patient's mandible in a precise way, the mandibular manipulator comprising:
a connecting frame comprising:
a first sliding incisor pull;
a second sliding incisor pull;
a first rotational member associated with the first sliding incisor pull; and
a second rotational member associated with the second sliding incisor pull, the connecting frame enabling the first sliding incisor pull and the second sliding incisor pull to be moved independently of one another with respect to the connecting frame by the first rotational member and the second rotational member, wherein each of the sliding incisor pulls comprises an associatable sliding member for interaction with the connecting frame at a slot and a cradle member associated with the sliding incisor pulls shaped to engage the patient's teeth and/or gums for manipulation of the mandible, and further wherein each rotational member is associated with the connecting frame at an aperture, and comprises a member or portion in physical contact with the associated sliding incisor pull at an interface therewith so as to change rotational motion of the rotational member to linear motion of the sliding incisor pulls and thus adjust each respective sliding incisor pull with respect to the connecting frame and the patient's mandible and thus manipulate the mandible in a longitudinal and vertical manner with respect to the patient's mouth, wherein the rotating members having a flange and creating linear motion of the incisor bites are locked in place by a threaded screw having a shoulder to produce a squeezing action between said shoulder and flange on the rotating member.

16. A mandibular manipulator comprising:
a frame comprising:
a first sliding incisor pull having a first cradle for receiving at least one of a subject's upper teeth and the subject's upper gums;
a second sliding incisor pull having a second cradle for receiving at least one of the subject's lower teeth and the subject's lower gums;
at least one rotational member associated with the first sliding incisor pull, the first rotational member configured for converting rotational motion of the rotational member to linear motion of the first sliding incisor pull; and a second rotational member associated with the second sliding incisor pull, the first rotational member configured for converting rotational motion of the rotational member to linear motion of the first sliding incisor pull, wherein the frame enables the first sliding incisor pull and the second sliding incisor pull to be moved independently of one another with respect to the frame by the first rotational member and the second rotational member to manipulate the subject's mandible in a longitudinal manner and a vertical manner, wherein each rotational member has a slip resistant surface adapted for grabbing.

17. The mandibular manipulator of claim 16, further comprising a third rotational member for converting rotational motion of the third rotational member to linear motion between a first portion of the frame and a second portion of the frame, wherein movement of the first portion of the frame relative to the second portion of the frame moves the first sliding incisor pull relative to the second sliding incisor pull in order to manipulate the subject's mandible in a third lateral direction.

18. A method of manipulating a mandible of a patient using the mandibular manipulator of claim 1, the method comprising:

rotating the first rotational member to linearly move the first sliding incisor pull relative to the connecting frame to position the mandible of the patient along a first axis of direction; and rotating the second rotational member to linearly move the second sliding incisor pull relative to the connecting frame to position the mandible of the patient along a second axis of direction perpendicular to the first axis of direction.

19. The method according to claim 18, further comprising rotating a third rotational member to linearly move the first sliding incisor pull relative to the second sliding incisor pull to position the mandible of the patient along a third axis of direction perpendicular to the first and second axes of direction.

20. A method of forming a mandibular manipulator, the method comprising:

slidably coupling a first incisor pull configured for linear movement in along a first axis of direction to a connecting frame;

coupling a first rotational member to the connecting frame for moving the first incisor pull along the first axis of direction;

positioning a cradle member of the first incisor pull for receiving a portion of a patient's teeth and/or gums spaced from the connecting from to provide space for the patient's lip;

slidably coupling a second incisor pull configured for linear movement in along a second axis of direction perpendicular to the first axis of direction to the connecting frame;

coupling a second rotational member to the connecting frame for moving the second incisor pull along the second axis of direction; and coupling a third rotational member for converting rotational motion of the third rotational member to linear motion between a first portion of the frame and a second portion of the frame such that movement of the first portion of the frame relative to the second portion of the frame moves the first sliding incisor pull relative to the second sliding incisor pull in order to manipulate the subject's mandible in a third lateral direction.

* * * * *